US012285625B2

(12) United States Patent
Schmidt

(10) Patent No.: US 12,285,625 B2
(45) Date of Patent: Apr. 29, 2025

(54) LIGHT THERAPY DEVICE THAT TREATS A SUBJECT WITH MULTIPLE WAVELENGTHS OF LIGHT

(71) Applicant: SOLETLUNA HOLDINGS, INC., San Diego, CA (US)

(72) Inventor: David Schmidt, San Diego, CA (US)

(73) Assignee: SOLETLUNA HOLDINGS, INC., San Diego, CA (US)

(*) Notice: Subject to any disclaimer, the term of this patent is extended or adjusted under 35 U.S.C. 154(b) by 0 days.

(21) Appl. No.: 18/918,326

(22) Filed: Oct. 17, 2024

(65) Prior Publication Data

US 2025/0041619 A1  Feb. 6, 2025

Related U.S. Application Data

(63) Continuation-in-part of application No. 18/332,879, filed on Jun. 12, 2023.

(51) Int. Cl.
*A61N 5/06* (2006.01)

(52) U.S. Cl.
CPC ........ *A61N 5/06* (2013.01); *A61N 2005/0638* (2013.01); *A61N 2005/0644* (2013.01); *A61N 2005/0647* (2013.01); *A61N 2005/0659* (2013.01); *A61N 2005/0661* (2013.01); *A61N 2005/0663* (2013.01); *A61N 2005/0667* (2013.01)

(58) Field of Classification Search
CPC .................... A61N 5/06; A61N 5/0616; A61N 2005/0636; A61N 2005/0638; A61N 2005/0639; A61N 2005/0644; A61N 2005/0647; A61N 2005/0651; A61N 2005/0661; A61N 2005/0662; A61N 2005/0666; A61N 2005/0667; A61N 5/067
USPC ......................... 607/81, 82, 88, 89
See application file for complete search history.

(56) References Cited

U.S. PATENT DOCUMENTS

| 4,930,504 | A | 6/1990 | Diamantopoulos | |
|---|---|---|---|---|
| 11,820,675 | B1* | 11/2023 | Schmidt | C02F 1/325 |
| 2004/0030370 | A1 | 2/2004 | Lytle | |
| 2009/0005839 | A1* | 1/2009 | Griffith | A61N 5/0614 |
| | | | | 607/91 |
| 2015/0265846 | A1 | 9/2015 | Baird et al. | |
| 2018/0250402 | A1* | 9/2018 | Deisseroth | A61N 5/06 |
| 2019/0209718 | A1* | 7/2019 | Church | B01J 19/123 |
| 2022/0001194 | A1* | 1/2022 | Johnson | A61N 5/0622 |

(Continued)

OTHER PUBLICATIONS

International Search Report, conducted on Oct. 11, 2024, for Application PCT/US2024/033557.

*Primary Examiner* — Ahmed M Farah
(74) *Attorney, Agent, or Firm* — ARC IP Law, PC; Joseph J. Mayo

(57) ABSTRACT

A light therapy device that treats a subject with multiple wavelengths of light to provide a beneficial therapeutic effect. The device may emit at least three different wavelengths that are selected from specific wavelength combinations that have been found to have synergistic and positive therapy effects. The lights may be incorporated into any type of therapy device, such as a handheld light therapy device, light therapy elements integrated into a hat for treating the scalp or for hair loss, a light therapy bed, a light therapy facial treatment device, and a light therapy sauna.

9 Claims, 16 Drawing Sheets

(56) References Cited

U.S. PATENT DOCUMENTS

| | | | |
|---|---|---|---|
| 2022/0280807 A1* | 9/2022 | van de Ven | A61N 5/0618 |
| 2024/0091551 A1* | 3/2024 | Cabana | A61N 5/067 |

\* cited by examiner

| | Wavelength 1 (nm) | Wavelength 2 (nm) | Wavelength 3 (nm) |
|---|---|---|---|
| Wavelength Set Option 1 | $\lambda_{11}$ 315, 630, 1260 | $\lambda_{12}$ 276, 551, 1102 | $\lambda_{13}$ 349, 698, 1396 |
| Wavelength Set Option 2 | 281, 561, 1122 | 246, 491, 982 | 310, 619, 1238 |
| Wavelength Set Option 3 | 266, 532, 1064 | 233, 466, 932 | 294, 587, 1174 |
| Wavelength Set Option 4 | 237, 473, 946 | 207, 414, 828 | 261, 522, 1044 |
| Wavelength Set Option 5 | 211, 421, 842 | 185, 369, 738 | 233, 465, 930 |
| Wavelength Set Option 6 | $\lambda_{21}$ 374, 748, 1496 | $\lambda_{22}$ 214, 427, 855 | $\lambda_{23}$ 339, 677, 1354 |
| Wavelength Set Option 7 | 280, 560, 1120 | 245, 490, 980 | 309, 618, 1239 |

FIG. 13
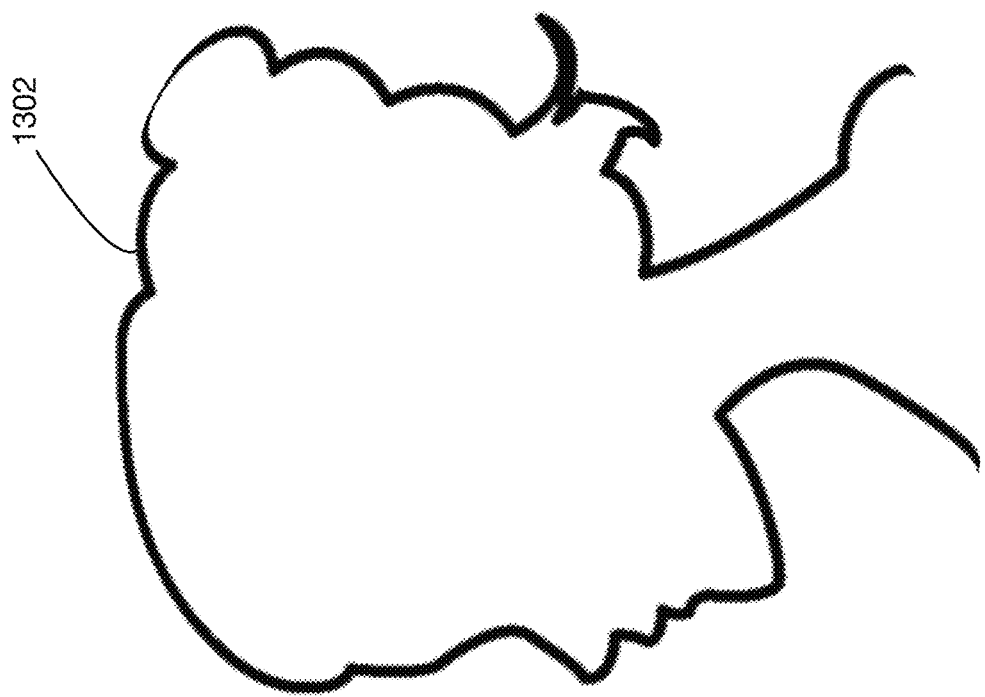
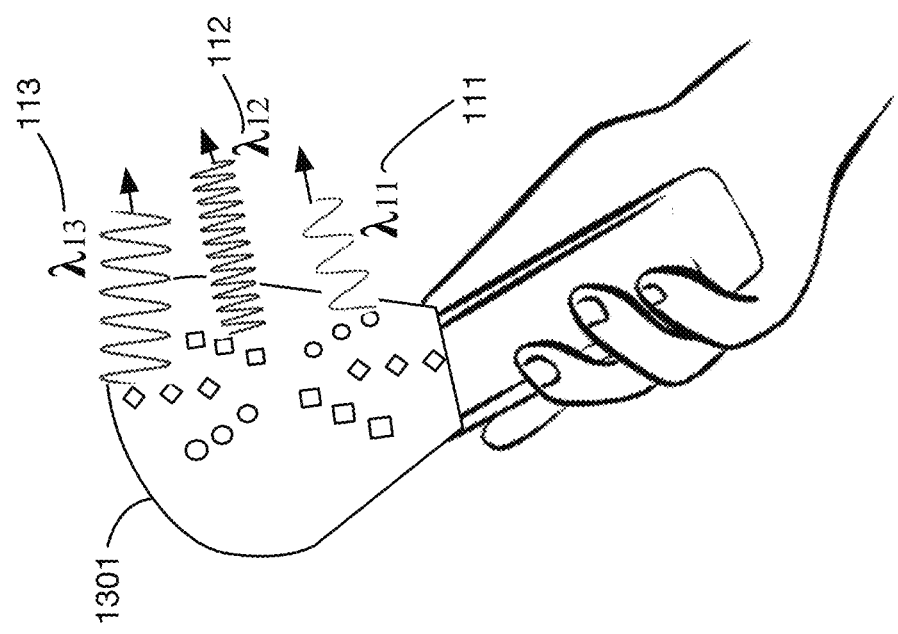

FIG. 14
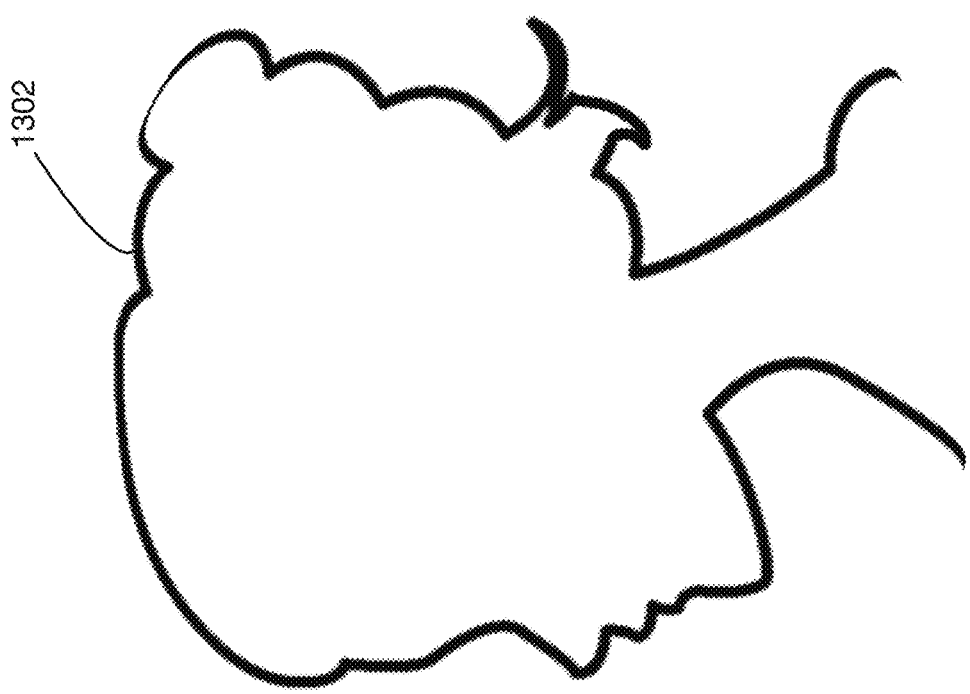
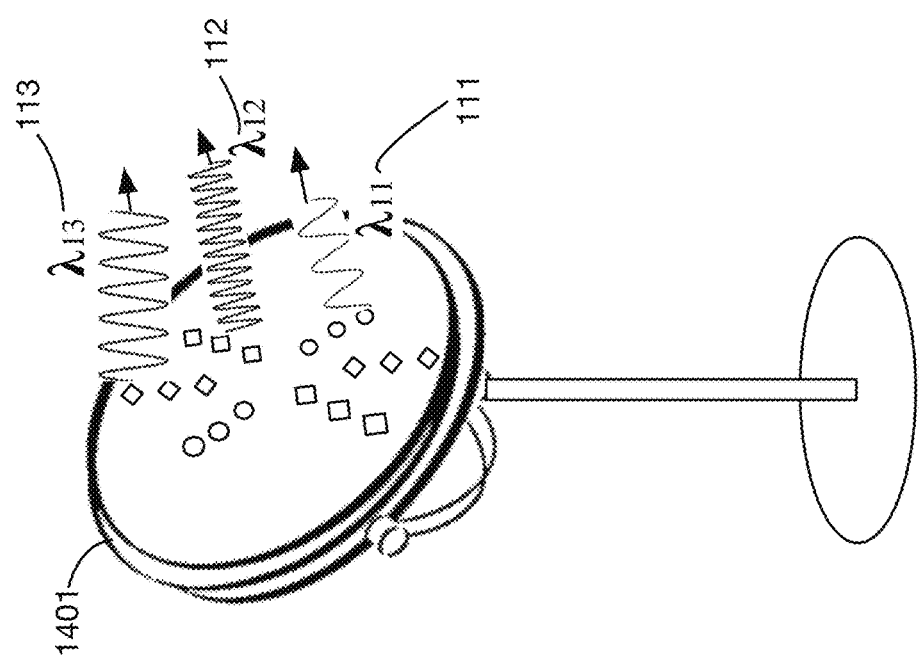

LIGHT THERAPY DEVICE THAT TREATS A SUBJECT WITH MULTIPLE WAVELENGTHS OF LIGHT

This application is a continuation in part of U.S. Utility patent application Ser. No. 18/332,879 filed 12 Jun. 2023, the specification of which is hereby incorporated herein by reference.

BACKGROUND OF THE INVENTION

Field of the Invention

One or more embodiments of the invention are related to the field of therapeutic devices that use light. More particularly, but not by way of limitation, one or more embodiments of the invention enable a light therapy device that treats a subject with multiple wavelengths of light from one direction or different directions.

Description of the Related Art

Light therapy devices may be used to treat various health conditions and to enhance well-being. Current light therapy devices typically use a single wavelength of light, which limits the benefits of the therapy.

For at least the limitations described above there is a need for a light therapy device that treats a subject with multiple wavelengths of light.

BRIEF SUMMARY OF THE INVENTION

One or more embodiments described in the specification are related to a light therapy device that treats a subject with multiple wavelengths of light. Embodiments of the invention may treat a subject with multiple wavelengths of light selected from specific groups of wavelengths that are known to work well in combination.

One or more embodiments of the invention may have a transparent container that contains water to be treated, a first light panel located on a first side of the container, and a second light panel located on a second side of the container. Alternatively, the first light panel may be located underneath the transparent container, and the second light panel located on top of the transparent container. The first light panel may have multiple light sources that emit light of three different first side wavelengths that is directed towards the water in the container. The second light panel may have multiple light sources that emit light of three different second side wavelengths that is directed towards the water in the container. The three different second side wavelengths may all be different from the three different first side wavelengths. In one or more embodiments one or more light panels may be utilized that transmit a plurality of wavelengths. For example, embodiments may utilize one light panel to treat a subject from a single direction. These embodiments may be lighter, less costly and utilize less power.

In one or more embodiments of the invention, the second side of the container may be opposite the first side. In one or more embodiments the first light panel may be above the transparent container and the second light panel may be below the transparent container.

In one or more embodiments of the invention, the amounts of light emitted from the first light panel in each of the three different first side wavelengths may be substantially equal, and the amounts of light emitted from the second light panel in each of the three different second side wavelengths may be substantially equal. In addition, the amount of light from each LED that emits a wavelength for a given light panel may be different. More specifically, for the three wavelengths of light per panel as described in this invention, the amount of light per LED may be in the ratio of 0.875:1:1.125. In other words, the number of LED's, or the total power in watts of the first LED in the series as described in this invention will be 0.875 units relative to 1 unit for the second LED and 1.125 units for the third LED. In practice, what this means is that for an LED panel of 27 watts, LED 1 will be about 7.9 watts, LED 2 will be about 9 watts and LED 3 will be about 10.1 watts. Other LED powers may be utilized for slower or faster processing of water or for larger or smaller containers.

In one or more embodiments of the invention, the three different first side wavelengths may be selected from a first wavelength set that is selected from multiple wavelength set options, and the three different second side wavelengths may be selected from a second wavelength set, different from the first wavelength set, that is selected from these wavelength set options. Each wavelength set option may have three different wavelength one options, three different wavelength two options, and three different wavelength three options. The three different first side wavelengths may include a first wavelength that is substantially equal to one of the three different wavelength one options associated with the first wavelength set, a second wavelength that is substantially equal to one of the three different wavelength two options associated with the first wavelength set, and a third wavelength that is substantially equal to one of the three different wavelength three options associated with the first wavelength set. The three different second side wavelengths may include a first wavelength that is substantially equal to one of the three different wavelength one options associated with the second wavelength set, a second wavelength that is substantially equal to one of the three different wavelength two options associated with the second wavelength set, and a third wavelength that is substantially equal to one of the three different wavelength three options associated with the second wavelength set.

In one or more embodiments of the invention, the wavelength set options may include a first wavelength set option with wavelength one options that include 315 nm, 630 nm, and 1260 nm, with wavelength two options that include 276 nm, 511 nm, and 1102 nm, and with wavelength three options that include 349 nm, 698 nm, and 1396 nm. The wavelength set options may include a second wavelength set option with wavelength one options that include 281 nm, 561 nm, and 1122 nm, with wavelength two options that include 246 nm, 491 nm, and 982 nm, and with wavelength three options that include 310 nm, 619 nm, and 1238 nm. The wavelength set options may include a third wavelength set option with wavelength one options that include 266 nm, 532 nm, and 1064 nm, with wavelength two options that include 233 nm, 466 nm, and 932 nm, and with wavelength three options that include 294 nm, 587 nm, and 1174 nm. The wavelength set options may include a fourth wavelength set option with wavelength one options that include 237 nm, 473 nm, and 946 nm, with wavelength two options that include 207 nm, 414 nm, and 828 nm, and with wavelength three options that include 261 nm, 522 nm, and 1044 nm. The wavelength set options may include a fifth wavelength set option with wavelength one options that include 211 nm, 421 nm, and 842 nm, with wavelength two options that include 185 nm, 369 nm, and 738 nm, and with wavelength three options that include 233 nm, 465 nm, and 930 nm. The wavelength set options may include a sixth wavelength set option with wavelength one options that include 374 nm, 748 nm, and 1496 nm, with wavelength two options that include 214 nm, 427 nm, and 855 nm, and with wavelength three options that include 339 nm, 677 nm, and 1354 nm. The wavelength set options may include a seventh wavelength set option with wavelength one options that include 280 nm, 560 nm, and 1120 nm, with wavelength two options that include 245 nm, 490 nm, and 980 nm, and with wavelength three options that include 309 nm, 618 nm, and 1239 nm.

In tabular form:

TABLE 1

| Wavelength Sets | |
|---|---|
| First wavelength set option | |
| wavelength one options that include | 315 nm, 630 nm, and 1260 nm, |
| wavelength two options that include | 276 nm, 511 nm, and 1102 nm, and |
| wavelength three options that include | 349 nm, 698 nm, and 1396 nm. |
| Second wavelength set option | |
| wavelength one options that include | 281 nm, 561 nm, and 1122 nm, |
| wavelength two options that include | 246 nm, 491 nm, and 982 nm, and |
| wavelength three options that include | 310 nm, 619 nm, and 1238 nm. |
| Third wavelength set option | |
| wavelength one options that include | 266 nm, 532 nm, and 1064 nm, |
| wavelength two options that include | 233 nm, 466 nm, and 932 nm, and |
| wavelength three options that include | 294 nm, 587 nm, and 1174 nm. |
| Fourth wavelength set option | |
| wavelength one options that include | 237 nm, 473 nm, and 946 nm, |
| wavelength two options that include | 207 nm, 414 nm, and 828 nm, and |
| wavelength three options that include | 261 nm, 522 nm, and 1044 nm. |
| Fifth wavelength set option | |
| wavelength one options that include | 211 nm, 421 nm, and 842 nm, |
| wavelength two options that include | 185 nm, 369 nm, and 738 nm, and |
| wavelength three options that include | 233 nm, 465 nm, and 930 nm. |
| Sixth wavelength set option | |
| wavelength one options that include | 374 nm, 748 nm, and 1496 nm, |
| wavelength two options that include | 214 nm, 427 nm, and 855 nm, and |
| wavelength three options that include | 339 nm, 677 nm, and 1354 nm. |
| Seventh wavelength set option | |
| wavelength one options that include | 280 nm, 560 nm, and 1120 nm, |
| wavelength two options that include | 245 nm, 490 nm, and 980 nm, and |
| wavelength three options that include | 309 nm, 618 nm, and 1239 nm. |

In other embodiments, the wavelength set may include two wavelength sets. The wavelength set options may include a first wavelength set option with wavelength one options that include 550 nm, 630 nm, and 710 nm. The second wavelength set options may include a first wavelength set option with wavelength one options that include 385 nm, 674 nm, and 866 nm. Water treated with these wavelength sets freezes in geometric shapes.

TABLE 2

| Wavelength Sets | |
|---|---|
| First wavelength set | |
| wavelength one options that include | 550 nm, 630 nm, and 710 nm. |
| Second wavelength set | |
| wavelength one options that include | 385 nm, 674 nm, and 866 nm. |

One or more embodiments of the invention may also have means for adding one or both of hydrogen and oxygen to the water before or during treatment. The Hydrogen may be added by using an electrolyzer, and then bubbling the Hydrogen into the water during the processing time of the water with the light panels. Alternatively, the Hydrogen may be added by using a material that contains Hydrogen. In one embodiment of the present invention the material that was selected is a Hydrogen contained within a silica cage, with this product having been invented by Patrick Flanagan and sold under the product name Crystal Energy®. Alternatively, the Hydrogen and Oxygen may be added from an electrolyzer, with both the Hydrogen and Oxygen being bubbled thru the water as the water is being processed by the light panels. Alternatively, the Hydrogen and Oxygen could be added with a material that contains Hydrogen and a material that contains Oxygen. Alternatively, the Hydrogen and Oxygen could be added by using a Browns Gas electrolyzer, and bubbled thru the water as the water is being treated by the light panel. Alternatively, the Hydrogen and Oxygen could be supplied from a PEM fuel cell. Alternatively, the Hydrogen and Oxygen could be supplied from tanks of stored gas.

One or more embodiments of the invention may enable a light therapy device that treats a subject with multiple wavelengths of light. The device may include multiple light sources configured to emit light of three different wavelengths that is directed towards a subject to be treated, such as a person or an animal. The three different wavelengths may be selected from a wavelength set that is selected from multiple wavelength set options. Each wavelength set option may have three different wavelength one options, three different wavelength two options, and three different wavelength three options. The three different wavelengths may include a first wavelength that is substantially equal to one of the three different wavelength one options associated with the wavelength set, a second wavelength that is substantially equal to one of the three different wavelength two options associated with the wavelength set, and a third wavelength that is substantially equal to one of the three different wavelength three options associated with the wavelength set.

In one or more embodiments of the light therapy device, the wavelength set options may include the options described above in Table 1.

In one or more embodiments of the light therapy device, the amounts of light emitted from the multiple light sources in each of the three different wavelengths may be substantially equal.

In one or more embodiments, the light therapy device may include a handheld therapy device.

In one or more embodiments, the light therapy device may be attached to or integrated into a hat, and the light of three different wavelengths may be directed towards the scalp of the subject to be treated.

In one or more embodiments, the light therapy device may include a light therapy bed on or within which the subject to be treated is located during therapy.

In one or more embodiments, the light therapy device may include a facial treatment therapy device, and the light of three different wavelengths may be directed towards the face of the subject to be treated.

In one or more embodiments, the light therapy device may include a light therapy sauna within which the subject to be treated is located during therapy.

BRIEF DESCRIPTION OF THE DRAWINGS

The above and other aspects, features and advantages of the invention will be more apparent from the following more particular description thereof, presented in conjunction with the following drawings wherein:

FIG. 13 shows an illustrative light therapy device in a handheld unit.

FIG. 14 shows an illustrative light therapy device used as a facial treatment.

DETAILED DESCRIPTION OF THE INVENTION

A light therapy device that treats a subject with multiple wavelengths of light will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 4:
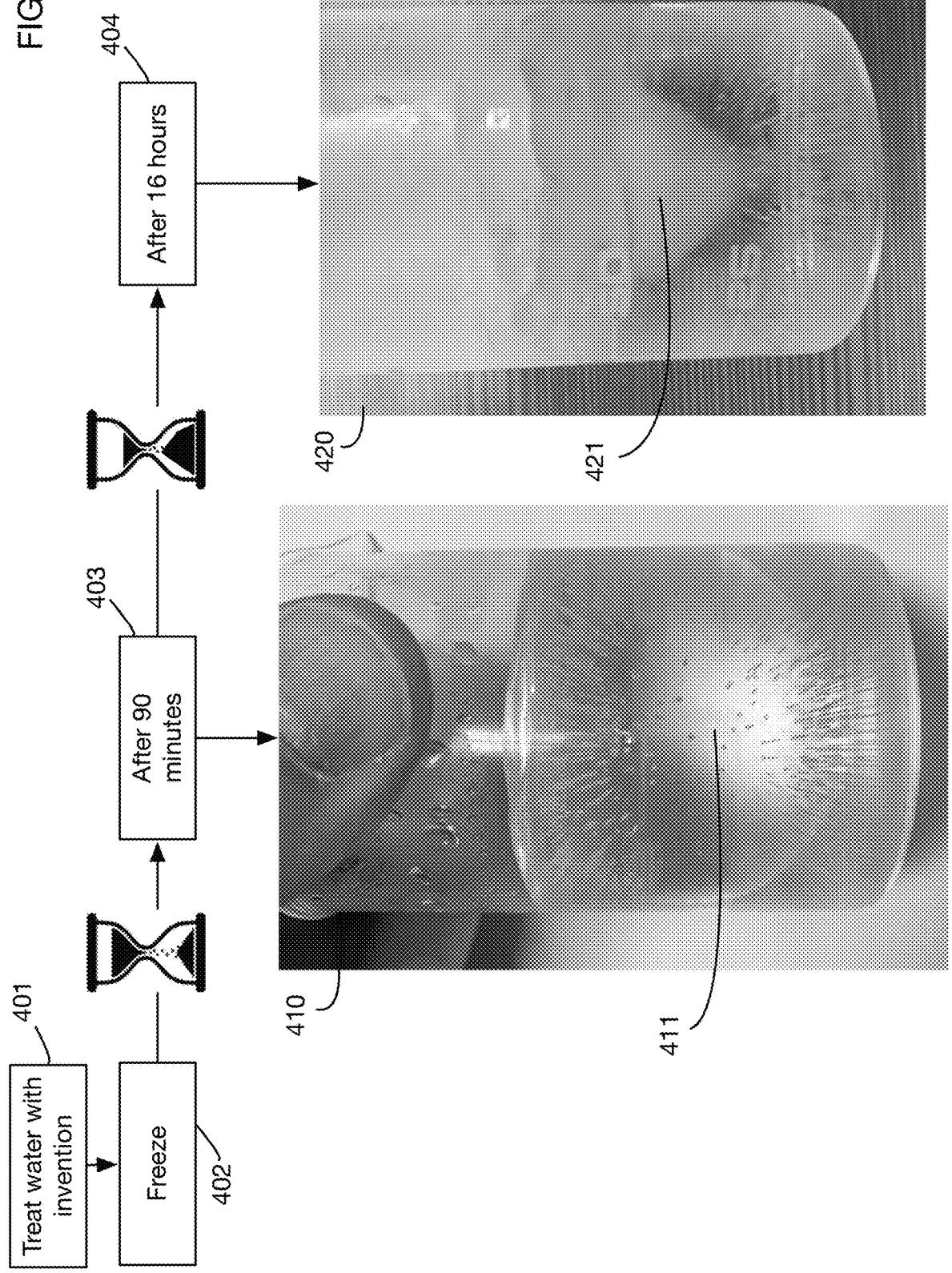
FIG. 4 shows images of results of an experiment that treated water using an embodiment of the invention; the crystal forms of the treated water when it was frozen demonstrate that the water had a novel structure.

Experiments conducted by the inventor have explored the use of specific wavelengths of light to create oscillations in the water which could progressively add energy to the water. Results appear to be optimal when water is treated with 6 different wavelengths of light. This type of treatment results in a novel water structure which may have additional energy in the water. FIG. 4 below shows illustrative results of an experiment that demonstrates this novel structure.

Figure 1:
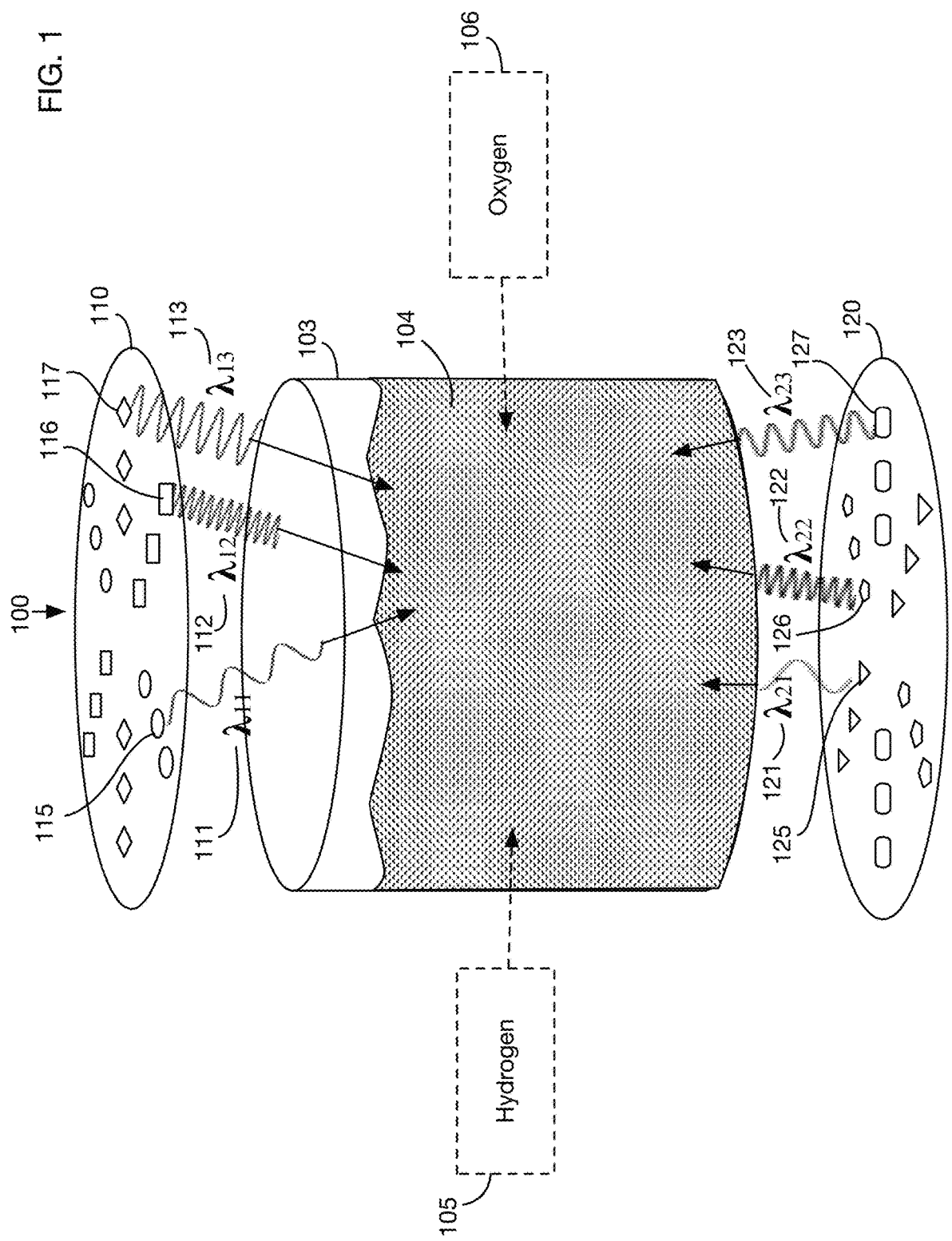
FIG. 1 shows a schematic of an illustrative embodiment of the invention that treats water using light of three different wavelengths emitted from each of two light panels.

FIG. 1 shows an illustrative device 100 that may be used to generate the desired structure of water. The device has a transparent container 103 that may hold water 104 to be treated. Container 103 may be of any shape and size. Two light panels 110 and 120 are located outside the container in different locations; for example, these panels may be on opposite sides of the container. In device 100, light panel 110 is located above the container 103, and light panel 120 is located below the container 103. The light panels may each contain multiple light sources, such as LEDs or lasers for example. Each light source may emit a specific wavelength or range of wavelengths of light that is directed towards the water 104 in container 103. The light emitted from the light sources interacts with water 104 and modifies its structure, as described below. In one or more embodiments of the invention, each of the light panels 110 and 120 may emit three different wavelengths of light, and the wavelengths from one panel may all be different from the wavelengths from the other panel; thus, the water may be treated with 6 different wavelengths. The different wavelengths may be emitted from different types of light sources, or from light sources that are controlled to emit these different types of wavelengths. In FIG. 1, the different light sources on panels 110 and 120 are indicated schematically by different shapes corresponding to different wavelengths; these icons do not necessarily indicate the actual shape of the light sources. Light panel 110 has 18 light sources, and light panel 120 has 18 light sources; these numbers are illustrative and embodiments may have any number of light sources on any light panel. Light source 115 emits light of wavelength 111; light source 116 emits light of wavelength 112; light source 117 emits light of wavelength 113; light source 125 emits light of wavelength 121; light source 126 emits light of wavelength 122; and light source 127 emits light of wavelength 123. The wavelengths 111, 112, 113, 121, 122, and 123 may all be different. In one or more embodiments the amount of light emitted in each wavelength may be substantially equal for each of the different wavelengths. For example, in panel 110 there are 6 light sources associated with each of the wavelengths 111, 112, and 113, and in panel 120 there are 6 light sources associated with each of the wavelengths 121, 122, and 123; each of these light sources may have similar or equal power or intensity. In one or more embodiments the light panels do not substantially output other wavelengths of light beyond the three different wavelengths emitted. For example, the light emitted may have a peak with fall off around a central frequency so that other frequencies are not emitted with an amplitude near the amplitude of the central frequency.

One or more embodiments of the invention may also provide a mechanism to add either or both of hydrogen 105 and oxygen 106 to water 104 before or during treatment by the light from panels 110 and 120. In one or more embodiments the hydrogen and oxygen may be generated by electrolysis of water, with the resulting hydrogen gas and oxygen gas bubbled through the water during treatment. An electrolyzer may be integrated into device 100. The hydrogen and oxygen generated during electrolysis may be kept in the same vessel 104. The hydrogen and oxygen may recombine into water when they are exposed to the light from the light panels. Instead of or in addition to electrolysis, any other source of hydrogen and/or oxygen gas may be used, and the gas may be bubbled through the water during treatment. Another source of hydrogen and/or oxygen that may be used in one or more embodiments is the introduction of compounds into the water that bear hydrogen and/or oxygen, such as hydrogen bound to a mineral or other complex.

An illustrative embodiment of device 100 may use for example a container 103 that is approximately 4 inches in diameter and 4 inches high and that holds approximately 500 ml of water, and panels 110 and 120 that are each be approximately 4 inches in diameter and may each consume approximately 20 watts of power. An illustrative treatment time for the water is 45 minutes. Additional sources of hydrogen and/or oxygen may or may not be used during treatment.

Figure 2:
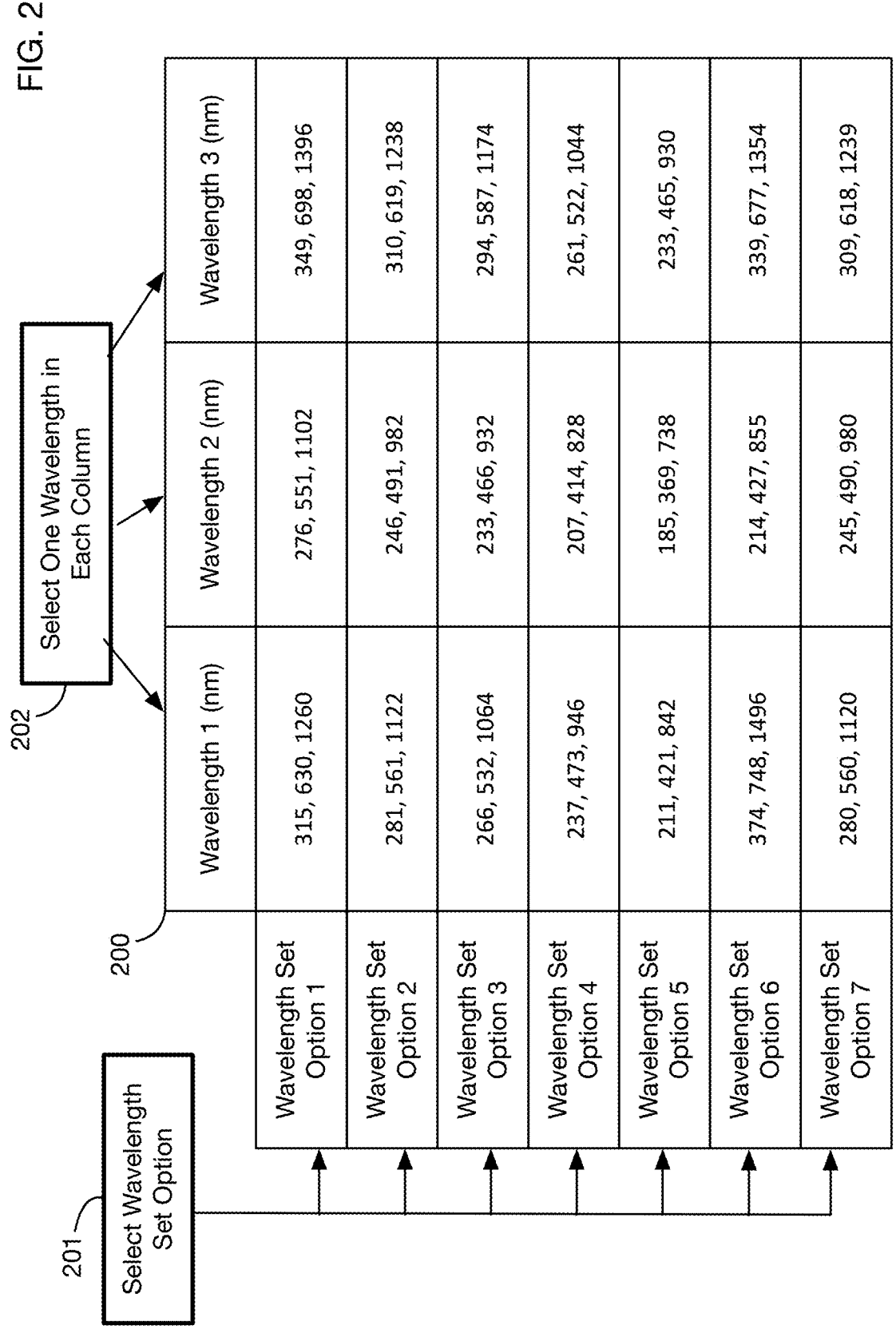
FIG. 2 shows illustrative options for wavelengths of light that may be used in one or more embodiments of the invention.

FIG. 2 shows illustrative wavelengths of light that may be used in one or more embodiments of device 100. In one or more embodiments, for each light panel a selection 201 may be made to select one of the 7 wavelength set options of table 200. Each light panel should be associated with a different wavelength set option. Then for each light panel, selection 202 may be made to choose one wavelength from each of the three columns of table 200. These wavelength selection steps 201 and 202 ensure that all wavelengths are different, and the specific wavelengths in the rows and columns of table 200 have been found experimentally to provide the desired results. The actual wavelengths used in an embodiment may differ from the ideal wavelengths shown in table 200, for example by approximately ±10 nm for each wavelength.

Figure 3:
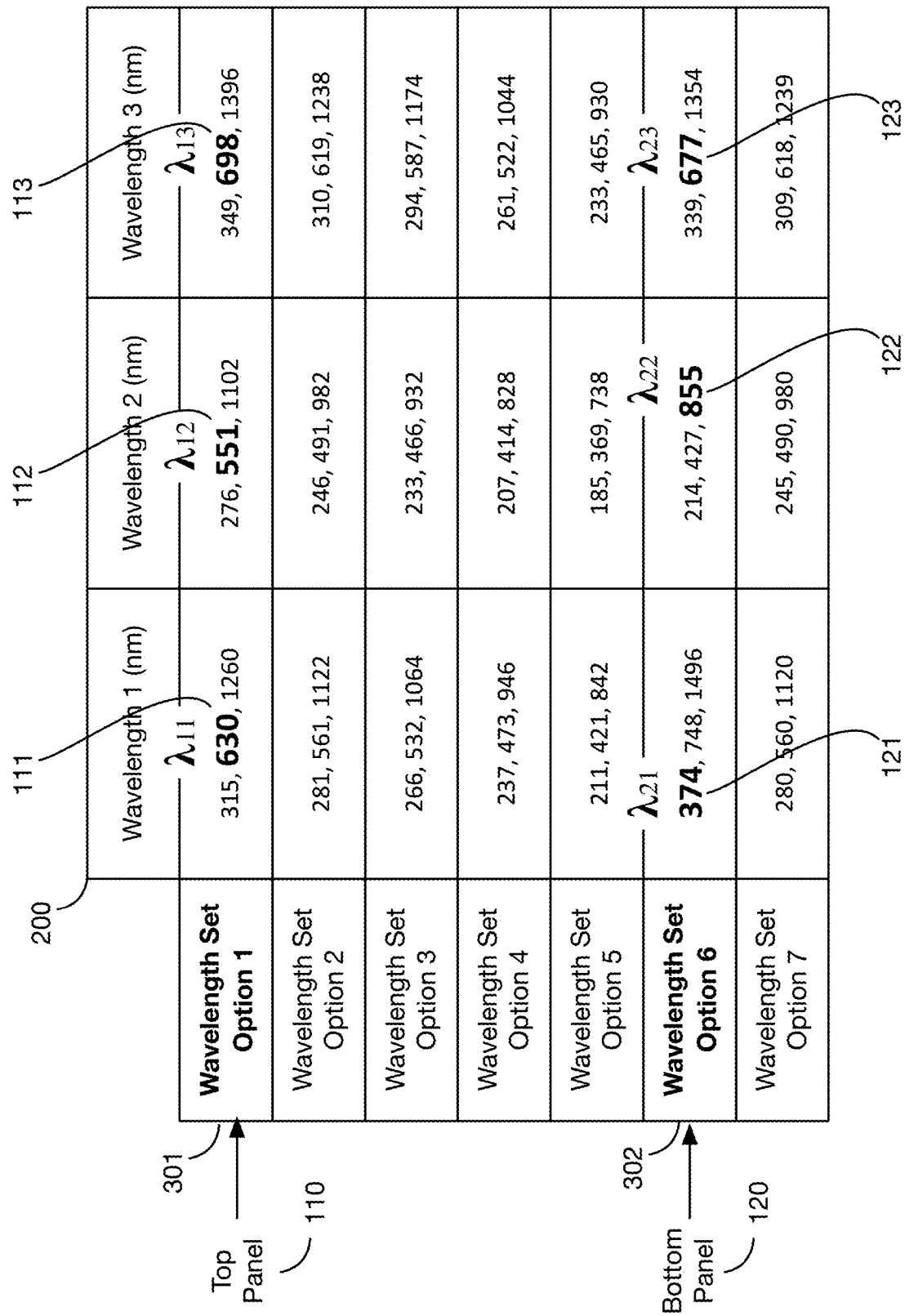
FIG. 3 shows an illustrative selection of 6 wavelengths from the options of FIG. 2 that may be used in one or more embodiments of the invention.

FIG. 3 shows an illustrative selection of wavelengths from table 200 for the light panels 110 and 120 and the wavelengths 111, 112, 113, 121, 122, 123 of device 100 of FIG. 1. In this example, light panel 110 is associated with wavelength option set 301, and light panel 120 is associated with wavelength option set 302. Any two wavelength option sets may be used. For panel 110, the first wavelength 111 is the second wavelength of the first column; the second wavelength 112 is the second wavelength of the second column, and the third wavelength 113 is the second wavelength of the third column. For panel 120, the first wavelength 121 is the first wavelength of the first column; the second wavelength 122 is the third wavelength of the second column, and the third wavelength 123 is the second wavelength of the third column. The illustrative selections are embodied in a device that treats water with 6 different wavelengths approximately equal to 630 nm, 551 nm, 698 nm, 374 nm, 855 nm, and 677 nm.

FIG. 4 shows results of an illustrative experiment performed by the inventor using an embodiment of the invention to treat water. In treatment step 401, 500 ml of water was placed into a glass container, with the glass container being about 4" in diameter and about 4" in height. One of the LED panels as described above was placed below the glass container, and the other was placed on top of the glass container so that both LED panels simultaneously treated the water in the glass container. The water was treated for 45 minutes.

After treatment in step 401, in step 402 the treated water was placed into a glass beaker which was then placed into a freezer. The water in the freezer was observed over the period of the next few hours as it froze. Image 410 shows the water at time 403 after 90 minutes, and image 420 shows the water at time 404 after 16 hours. What was noticed is that an implosion bubble 411 appears in image 410, and the resulting frozen ice has a water vortex 421 frozen inside in image 420. These unusual structures, which have not been previously observed in water, indicate that the structure of the water was altered by the treatment.

Figure 5:
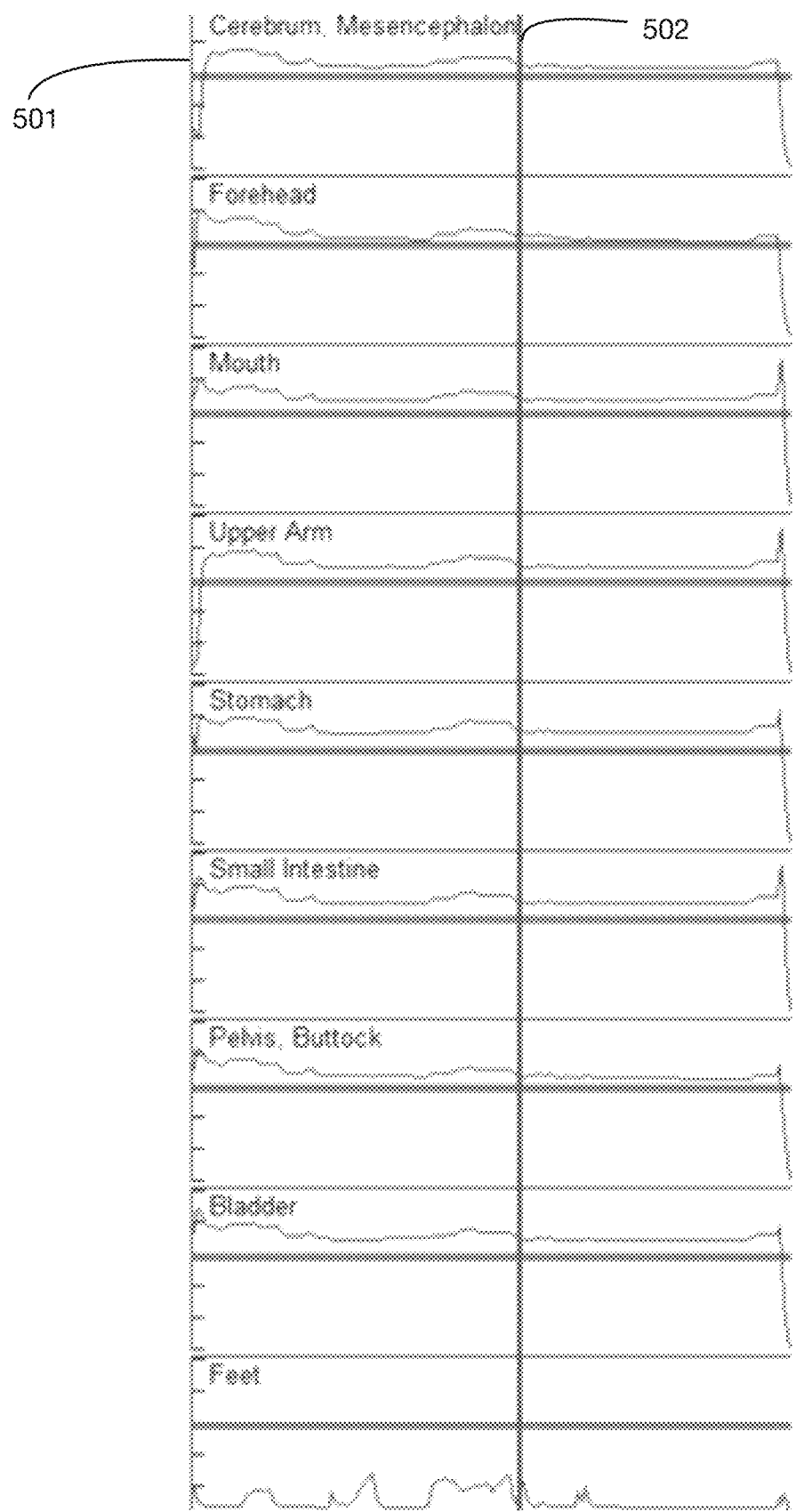
FIG. 5 shows results of an experiment in which a test subject drank water treated using an embodiment of the invention.

FIG. 5 shows the results of an experiment in which a test subject drank 500 ml of water that had been treated using an embodiment of the invention. Graphs 501 show a portion of a Biopulsar® recording of the subject, with the blue line 502 indicating the time at which the subject drank the treated water. The result was immediate (under 10 seconds) as well as systemic; the subject's readings became much more stable across multiple organ systems after drinking the treated water.

Figure 6:
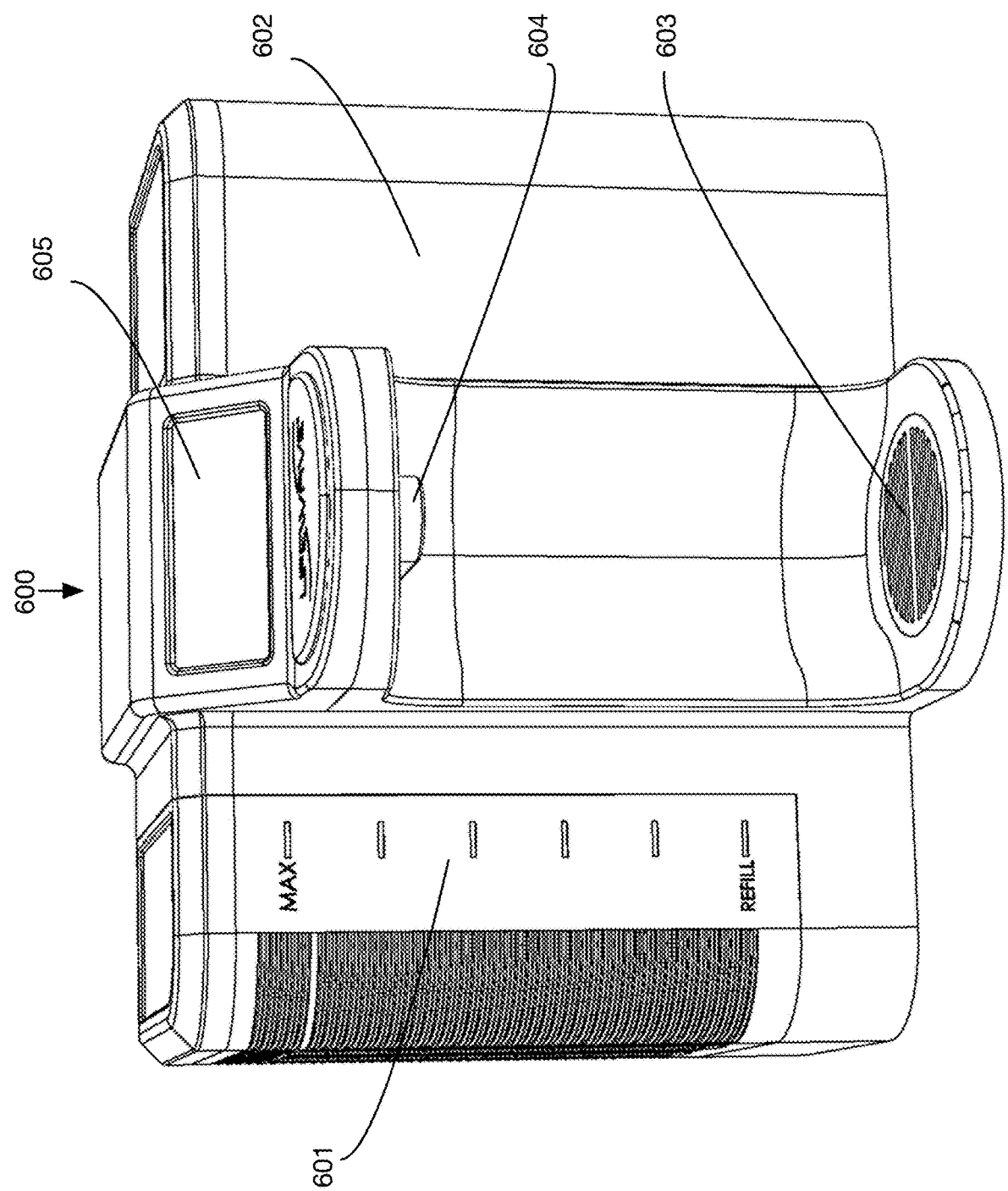
FIG. 6 shows an illustrative water treatment device that treats water with light and then dispenses treated water on demand into a container for drinking, such as a cup or water bottle.

In one or more embodiments, the invention may be incorporated into a device that treats and dispenses water. The device may for example maintain a stock of treated water that can be dispensed on demand, and dispensing may trigger treatment of additional water to be ready for a subsequent dispensing cycle. FIG. 6 shows an illustrative treatment and dispensing device 600. This device has a reservoir 601 that is filled by a user with untreated water. Lights and other components are contained within the housing 602. When a user wants to obtain treated water, the user may place a container such as a cup or water bottle into dispensing area 603 and use the control panel 605 to initiate dispensing of treated water from output 604. Control panel 605 may also include indicators of the device status, showing for example when components need to be replaced or refilled. Because treating water may take considerable time (such as 45 minutes, for example), the device may treat water in advance and hold treated water in one or more tanks to be ready for dispensing.

Figure 7:
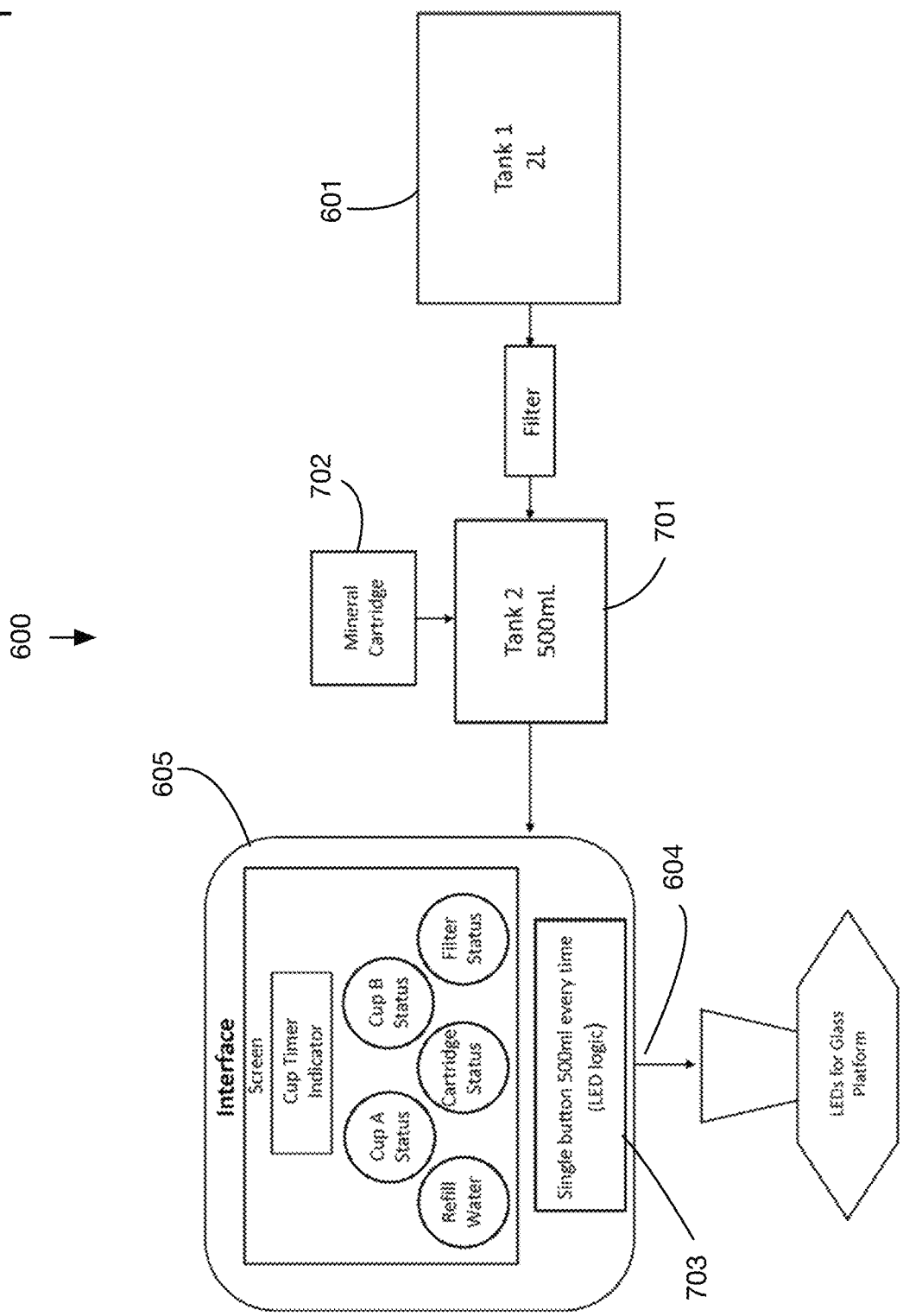
FIG. 7 shows an architectural diagram of selected components of the treatment and dispensing device of FIG. 6.
Figure 8:
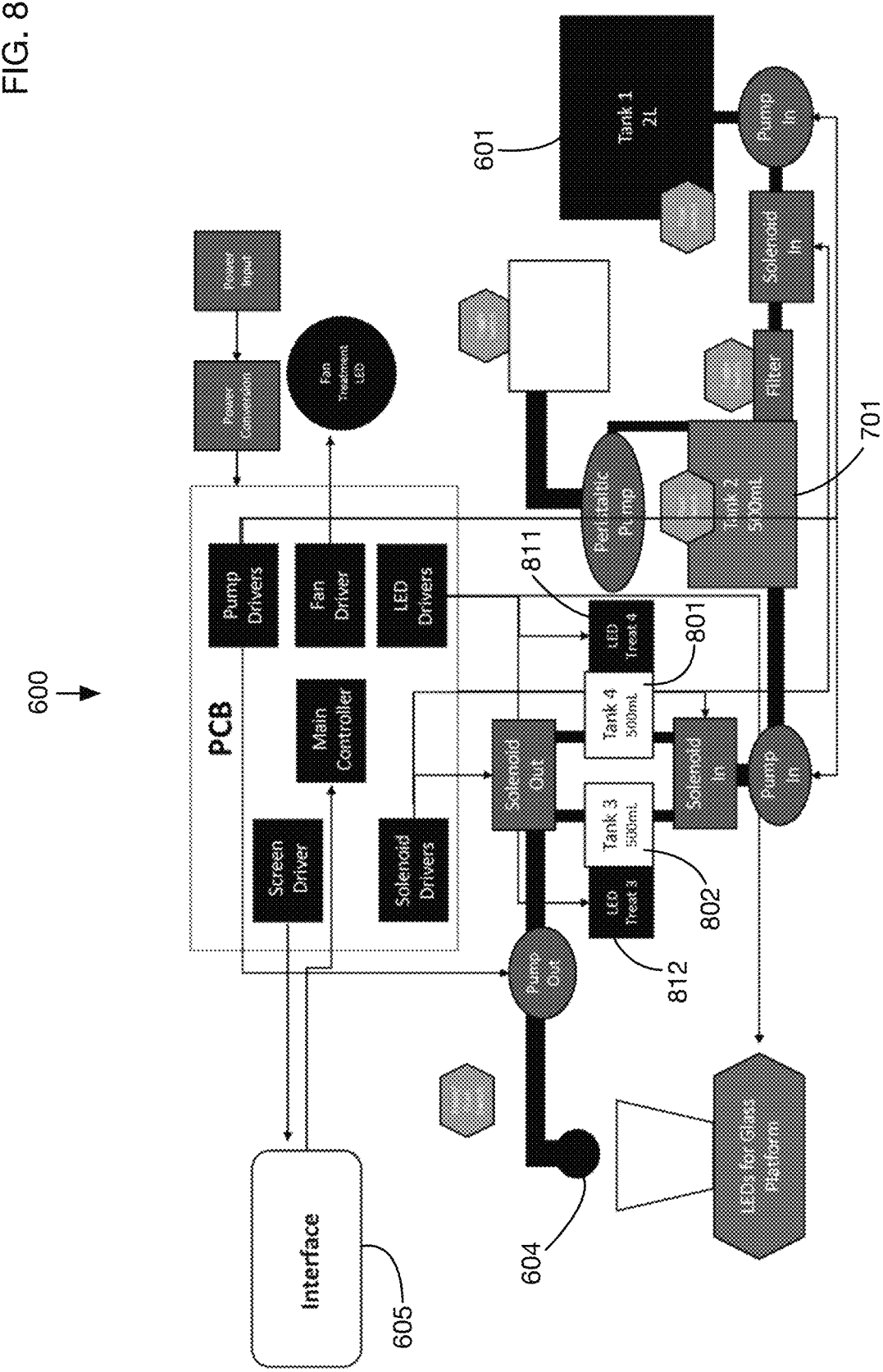
FIG. 8 shows a more detailed architectural diagram of components of the treatment and dispensing device of FIG. 6.

FIG. 7 shows a block diagram of selected illustrative components of device 600. Tank 601 that a user fills with untreated water may be for example 2 L in capacity. (This is illustrative; the device and the capacity of its tanks and reservoirs may be of any size.) This illustrative device treats 500 mL of water per cycle. In the initial treatment step, 500 mL is pumped from the tank 601 through a filter to tank 701, and minerals are added to the water from cartridge 702. After infusing the water with the minerals, subsequent steps treat the mixture with light (as shown in FIG. 8). Control panel 605 may provide indicators that the water filter or mineral cartridge 702 need to be replaced, and it may indicate that the tank 601 needs to be refilled. Panel 605 may also indicate when water is ready to be dispensed (after treatment), and how long a user may need to wait until the next dispensing cycle. When water is ready to be dispensed, the user may press button 703 to dispense 500 ml of treated water from output 604.

FIG. 8 shows a more detailed block diagram of components of device 600. The device has 4 tanks: reservoir 601 that holds untreated water, tank 701 where minerals are added to the water, and two light treatment tanks 801 and 802 with associated LED panels 811 and 812, respectively. Water is pumped from reservoir 601 to tank 701 where minerals are added, and then into tanks 801 and 802 where the water/mineral mixture is treated with light. Treated water can be dispensed from either tank 801 or 802. In one or more embodiments, LED panels 811 or 812 or both include at least one filter situated between the first light panel and the water that allows primarily only the wavelengths of the first wavelength set option or the second wavelength set option through while substantially blocking other wavelengths. In other embodiments, the filters may optionally be separate from the panels, i.e., not coupled to them but situated in proximity to them.

Figure 9:
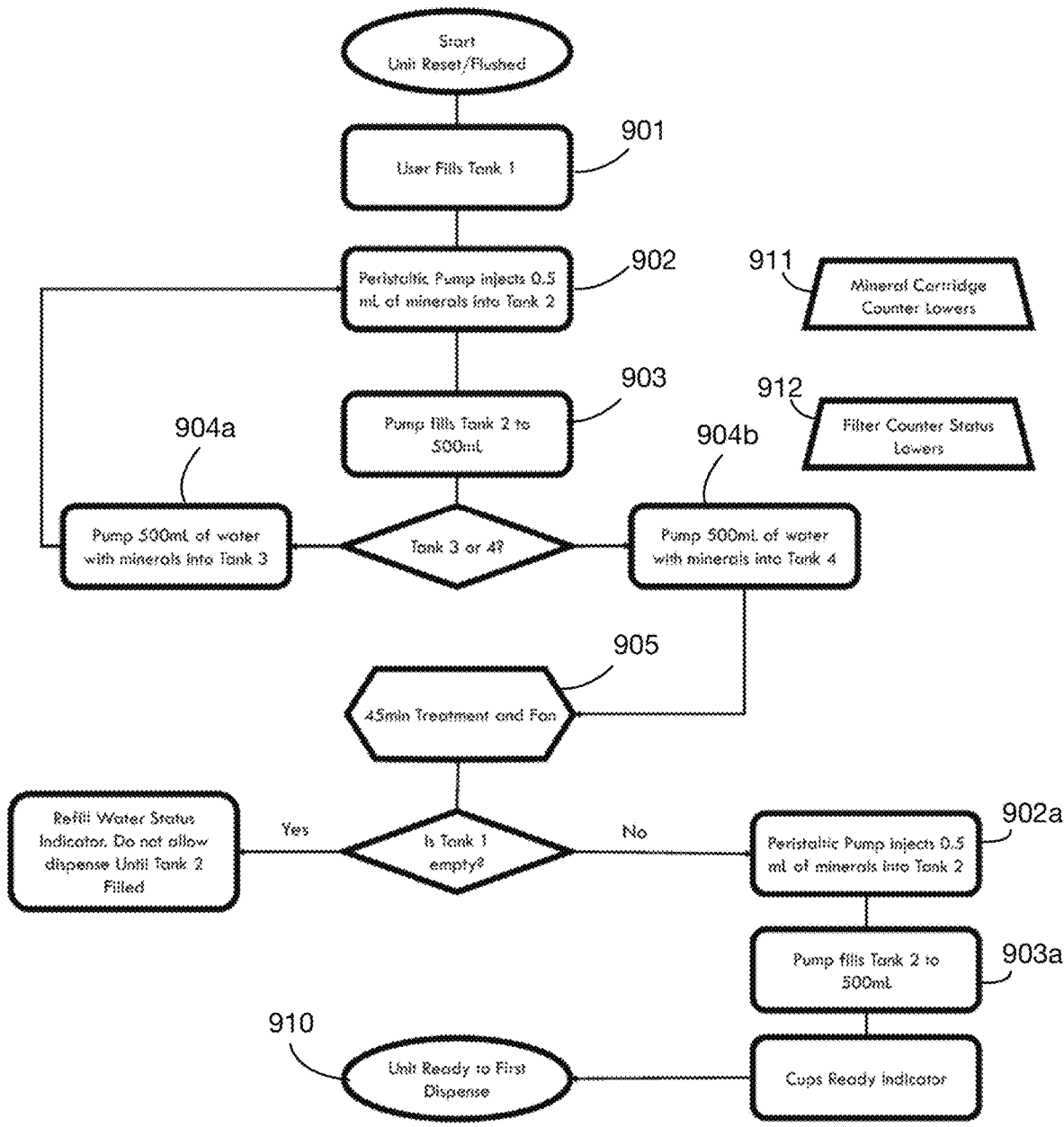
FIG. 9 shows a flowchart of treatment steps performed by the device of FIG. 6.
Figure 10:
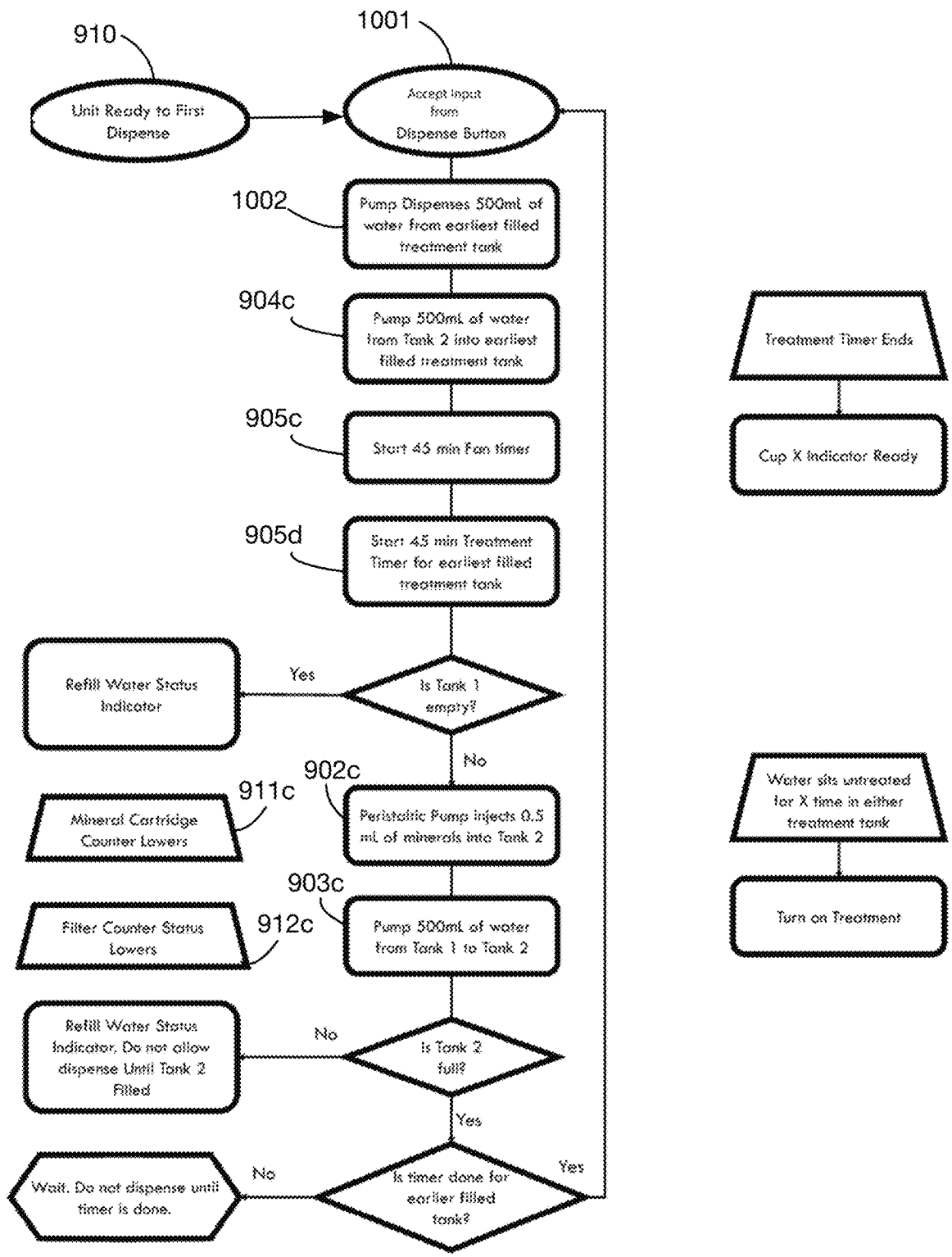
FIG. 10 continues the flowchart of FIG. 9 to show dispensing of treated water followed by another cycle of water treatment to prepare for a next dispensing cycle.

FIGS. 9 and 10 show flowcharts of illustrative steps performed by device 600 to treat and dispense water. FIG. 9 shows treatment steps that prepare water for initial dispensing. FIG. 10 shows an additional treatment cycle that occurs after dispensing, to prepare for the next dispensing cycle. In step 901, the user fills the reservoir 601 with untreated water. In step 902, a quantity of mineral (such as 0.5 mL) is injected into tank 701, and in step 903, 500 mL of water is added to tank 701. (Quantities are illustrative.) In step 904a, the water/mineral mixture is pumped to light treatment tank 802. Steps 902 and 903 are then repeated, and step 904b pumps the water/mineral mixture to light treatment tank 801. Step 905 then applies light to both tanks 801 and 802, for example for 45 minutes. If there is remaining water in reservoir 601, steps 902a and 903b repeat filling of tank 701 and adding mineral, to prepare for the next light treatment cycle. Event 910 then indicates (for example on the display panel) that the device is ready to dispense treated water. The system may also maintain counters of the number of uses of the water filter and mineral cartridge and may modify these counters in steps 911 and 912 when water flows through the filter and when mineral is injected from the mineral cartridge; these counters enable the device to indicate when the filter or mineral cartridge needs to be replaced.

Continuing in FIG. 10, when the user presses the button in step 1001 to dispense treated water, the device dispenses water in step 1002 from either tank 801 or 802 (depending on which was treated first). Steps 904c, 905c, 905d, 902c, 903c, 911c, and 912c then repeat mineral mixing and light treatment to refill the tank that was emptied in step 1002. These steps enable the device to have treated water available on demand, as long as the user does not dispense more rapidly than the system can treat.

Figure 11:
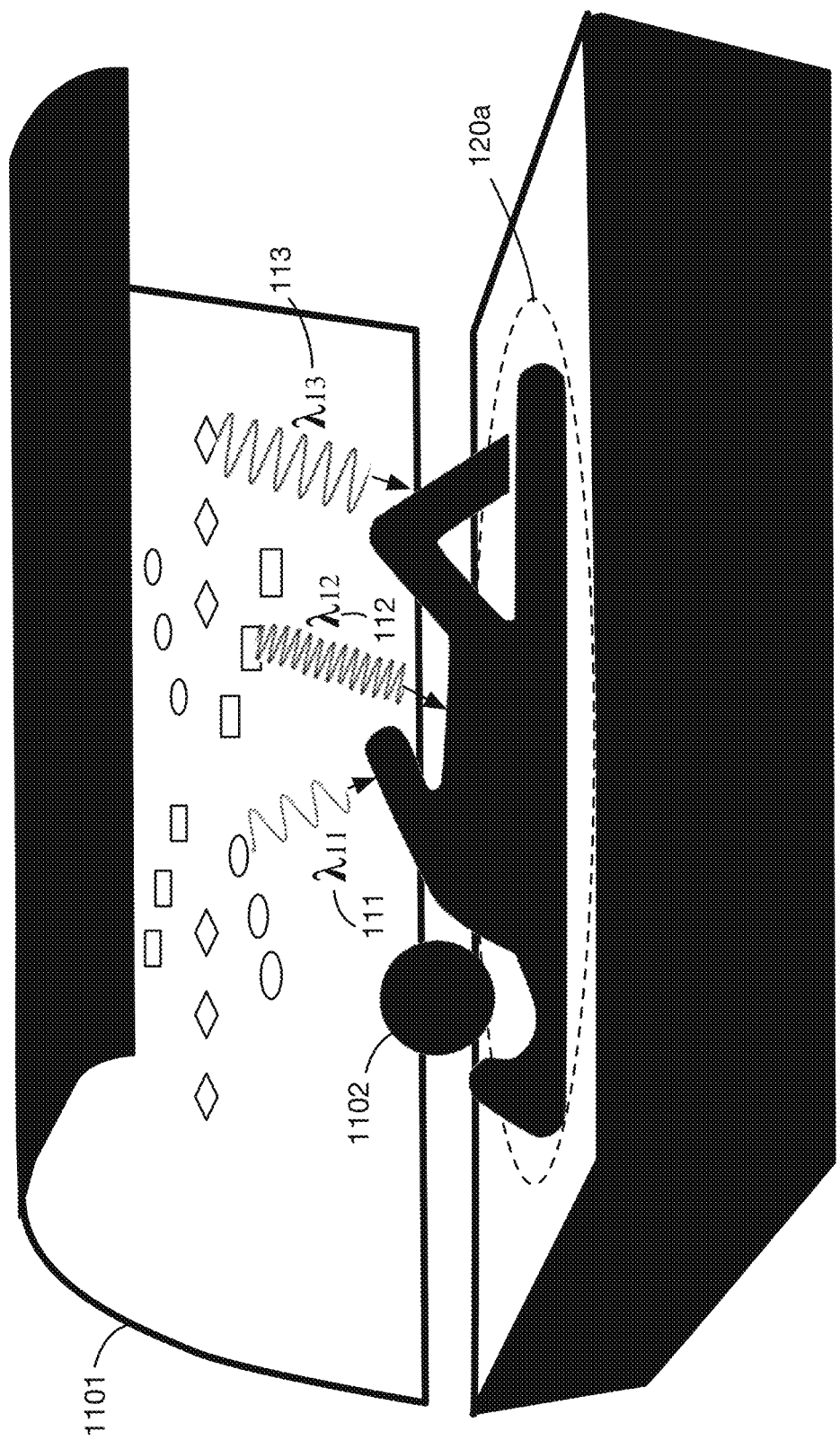
FIG. 11 shows an illustrative light therapy device similar to a tanning bed that treats a person with multiple wavelengths of light that may be similar to those used in a water treatment device.

The inventor has discovered that the wavelengths used in a water treatment device may be beneficial in a light therapy device that treats a subject such as a person or an animal. Since human bodies are primarily water, directing the wavelengths described above at the skin of a person may have effects on the water in the body, or on other tissues. FIG. 11 shows an illustrative light therapy device 1101 that treats a subject 1102 using the multiple wavelengths described above. This illustrative embodiment resembles a tanning bed. One or more embodiments of the invention may incorporate lights that emit multiple wavelengths into any type of light therapy device that directs light at a subject. Illustrative examples of light therapy devices may include for example, without limitation, handheld light therapy devices, light therapy incorporated into a hat (for example for treating the scalp or as a treatment for hair loss), light therapy beds a subject is on or within for treatment, light therapy facial treatment devices (which direct light towards the face), and light therapy saunas a subject is within for treatment. Any device that directs light at a subject for therapy may incorporate any of the wavelengths described in this specification. A light therapy device enabled by the invention may direct light at any part or parts of a subject's body. Light may be shine directly onto the subject's skin, or light may affect the skin indirectly such as through clothing.

Light therapy device 1101 has multiple lights on the inner surface of the top lid of the device. The lights may be integrated into or attached to the device. Lights may be placed in any locations and may emit light in any directions. In this illustrative embodiment, light from the lights in the top lid is directed downward towards the skin of subject 1102 who lies on the lower part of the light therapy bed. The lights in device 1101 may be similar for example to those of panel 110 in water treatment device 100 of FIG. 1. These lights may emit light of three or more wavelengths 111, 112, and 113. These wavelengths may be selected for example from the wavelength set options described above in Table 1. Device 1101 may have any number of lights for each wavelength, of any size and power. In one or more embodiments the amounts of light emitted in each wavelength may be substantially equal. Other embodiments may utilize one light source that outputs three different frequencies of light.

In one or more embodiments of the invention, the light therapy device may have additional light panels with other wavelengths. For example, light therapy device 1101 may have lights incorporated into a panel 120a located below the subject 1102. Light therapy devices may have any number of light panels that emit light in any desired directions. Each may have any number of lights. In one or more embodiments a second light panel may emit light in wavelengths selected from the wavelength set options described above in Table 2; in one or more embodiments these wavelengths of a second light panel may differ from the wavelengths of other lights in the device. In other embodiments, the wavelengths from two or more lights may be the same.

Figure 12:
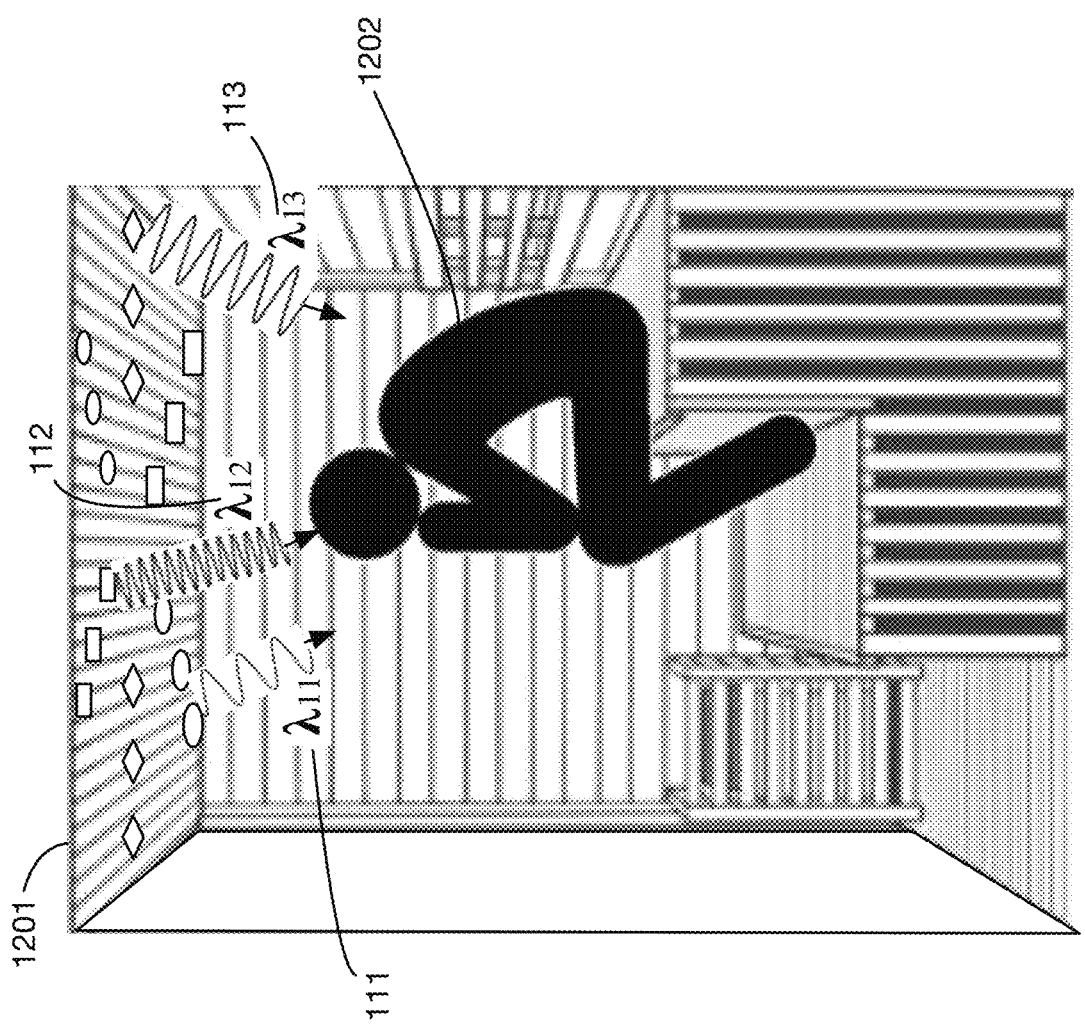
FIG. 12 shows an illustrative light therapy device integrated into a sauna.
Figure 15:
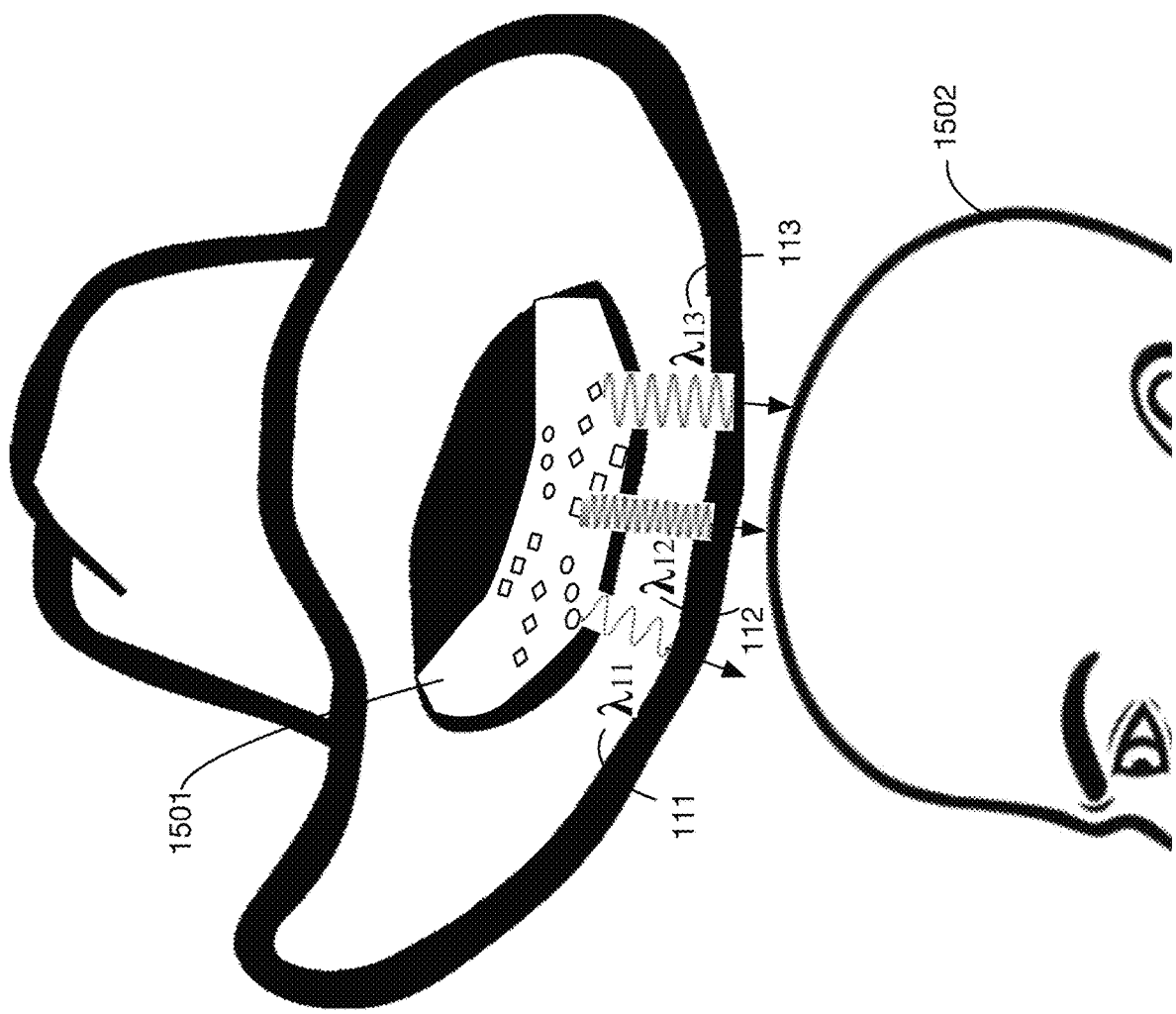
FIG. 15 shows an illustrative light device integrated into a hat to treat the scalp or hair.
Figure 16:
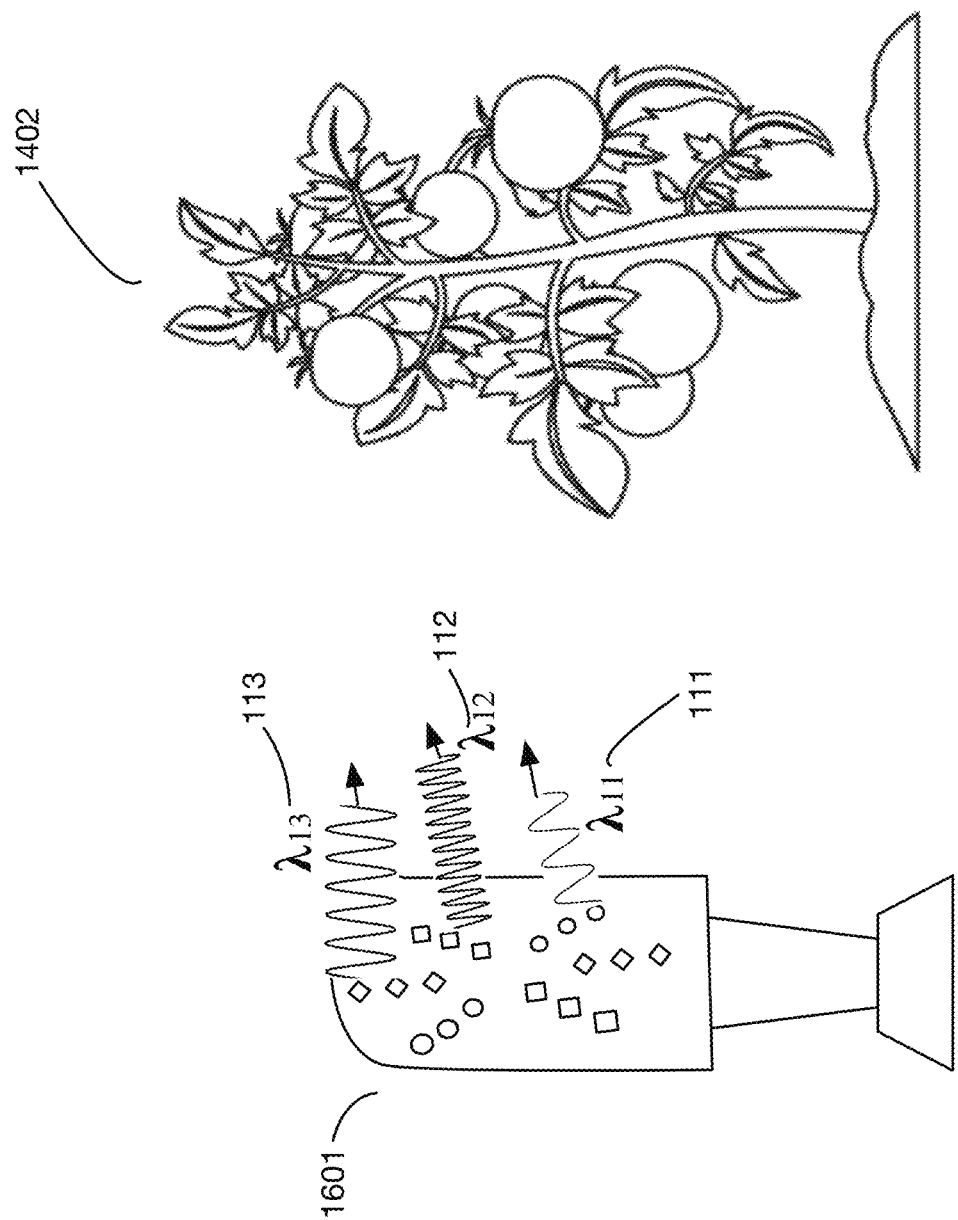
FIG. 16 shows an illustrative light device used for agricultural treatment.

Light therapy devices may have any size, shape, and form factor and may be used to treat any part or parts of a subject. They may be integrated into or attached to any other therapy devices or systems. FIG. 12, FIG. 13, FIG. 14, FIG. 15 and FIG. 16 show other illustrative embodiments of a light therapy device that uses multiple wavelengths of light. FIG. 12 shows a light therapy device 1201 that is similar to a sauna, or that is integrated into a sauna. This device has lights that direct three wavelengths 111, 112, and 113 at a subject 1202 who may sit, stand, or lie in the sauna. FIG. 13 shows an illustrative handheld light therapy device 1301 that may be held by subject 1302 or by another person treating subject 1302; device 1301 also emits three wavelengths 111, 112, and 113. FIG. 14 shows an illustrative facial treatment light therapy device 1401 that directs light of wavelengths 111, 112, and 113 at the face of subject 1302. FIG. 15 shows an illustrative light therapy device 1501 integrated into a hat, for example on the inside, that directs wavelengths 111, 112, and 113 at the scalp or hair of a subject 1502, for example as a treatment for hair loss. FIG. 16 shows an illustrative plant treatment light therapy device 1601 that directs light of wavelengths 111, 112, and 113 at a plant 1602.

In one or more embodiments, filters maybe coupled with or situated in front light therapy device 1101, 1201, 1301, 1401, 1501, 1601 that allows primarily only the wavelengths of the first wavelength set option or the second wavelength set option through while substantially blocking other wavelengths. In other embodiments, the filters may optionally be separate from the panels, i.e., not coupled to them but situated in proximity to them, as previously described with respect to LED panels 811 and 812.

While the invention herein disclosed has been described by means of specific embodiments and applications thereof, numerous modifications and variations could be made thereto by those skilled in the art without departing from the scope of the invention set forth in the claims.

What is claimed is:

1. A light therapy device that treats a subject with multiple wavelengths of light, comprising:
    a one or more light sources configured to emit light of three different wavelengths that is directed towards a subject to be treated,
        wherein said subject comprises a person or an animal;
        wherein said light that is emitted is configured to directly shine onto a skin of said subject, or indirectly shine onto said skin of said subject,
            to effect water in a body of said subject or on tissues of said subject via said three different wavelengths; wherein
    said three different wavelengths are selected from a wavelength set selected from a plurality of wavelength set options;
    each wavelength set option of said plurality of wavelength set options comprises said three different wavelengths;
    three different wavelength one options;
    said one or more light sources do not emit other wavelengths of light and,
    wherein said plurality of wavelength set options comprises
        a first wavelength set option comprising
            said three different wavelengths comprising 550 nm, 630 nm, and 710 nm;
        a second wavelength set option comprising
            said three different wavelengths comprising 385 nm, 674 nm, and 866 nm.

2. The light therapy device that treats a subject with multiple wavelengths of light of claim 1, wherein
    amounts of said light emitted from said one or more light sources in each of said three different wavelengths are equal.

3. The light therapy device that treats a subject with multiple wavelengths of light of claim 1, wherein said light therapy device comprises a handheld therapy device.

4. The light therapy device that treats a subject with multiple wavelengths of light of claim 1, wherein
    said light therapy device is attached to or integrated into a hat; and,
    said light of said three different wavelengths is directed towards a scalp of said subject to be treated.

5. The light therapy device that treats a subject with multiple wavelengths of light of claim 1, wherein said light therapy device comprises a light therapy bed on or within which said subject to be treated is located during therapy.

6. The light therapy device that treats a subject with multiple wavelengths of light of claim 1, wherein
    said light therapy device comprises a facial treatment therapy device; and,
    said light of said three different wavelengths is directed towards a face of said subject to be treated.

7. The light therapy device that treats a subject with multiple wavelengths of light of claim 1, wherein said light therapy device comprises a light therapy sauna within which said subject to be treated is located during therapy.

8. The light therapy device that treats a subject with multiple wavelengths of light of claim 1, wherein said light therapy device is directed at a plant.

9. The light therapy device that treats a subject with multiple wavelengths of light of claim 1, further comprising at least one filter coupled with or situated between said one or more light sources and said subject that allows primarily only wavelengths of said first wavelength set option or said second wavelength set option through said at least one filter while blocking other wavelengths.

* * * * *